United States Patent [19]

Sugiyama et al.

[11] Patent Number: 4,994,032
[45] Date of Patent: Feb. 19, 1991

[54] BALLOON CATHETER

[75] Inventors: Yoshiaki Sugiyama; Kyuta Sagae; Susumu Tanabe, all of Fuji, Japan

[73] Assignee: Terumo Kabushiki Kaisha, Tokyo, Japan

[21] Appl. No.: 277,564

[22] Filed: Nov. 29, 1988

[30] Foreign Application Priority Data

Dec. 1, 1987 [JP] Japan ................................ 62-303930

[51] Int. Cl.⁵ ............................................ A61M 25/10
[52] U.S. Cl. ...................................... 604/96; 604/288; 606/194
[58] Field of Search .................................. 604/96–103, 604/282, 192–196; 128/344

[56] References Cited

U.S. PATENT DOCUMENTS

| 4,571,240 | 2/1986 | Samson et al. | 604/96 |
| 4,597,755 | 7/1986 | Samson et al. | 604/96 |
| 4,646,719 | 3/1987 | Neumann et al. | 128/344 |
| 4,782,834 | 11/1988 | Maguire et al. | 604/96 |

Primary Examiner—Stephen C. Pellegrino
Attorney, Agent, or Firm—Frishauf, Holtz, Goodman & Woodward

[57] ABSTRACT

There is provided a balloon catheter comprising a tubular body including at least one lumen, and a foldable balloon provided at a predetermined distal portion on the outer surface of said tubular body so that the balloon communicates with at least one lumen in said tubular body, wherein reinforcement is provided at a predetermined portion on the outer surface of said tubular body surrounded by said balloon. The reinforcement is preferably formed on an X-ray opague material and in the form of a coil.

13 Claims, 7 Drawing Sheets

FIG.1
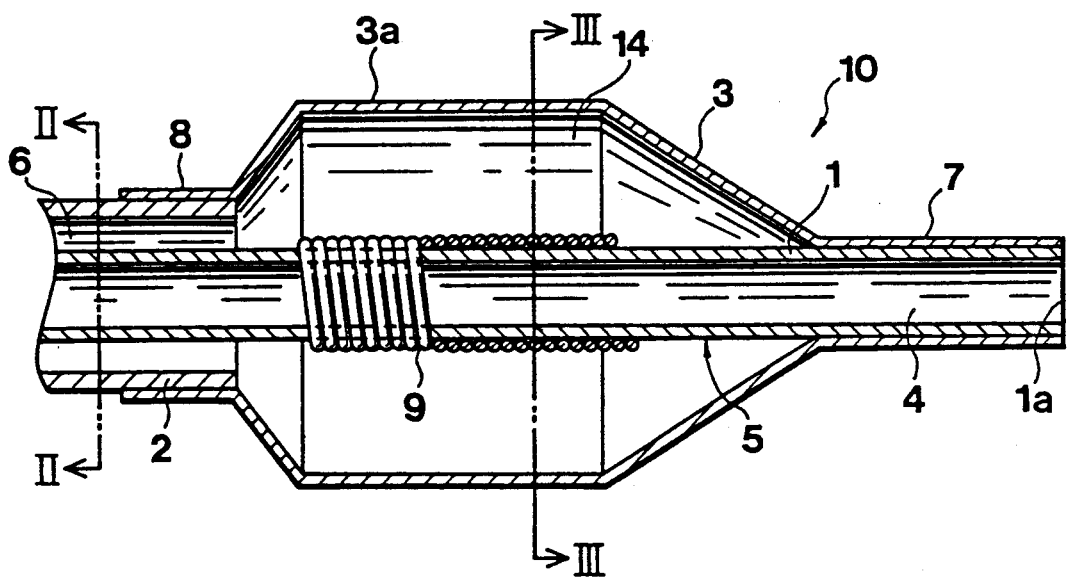
FIG.2
FIG.3
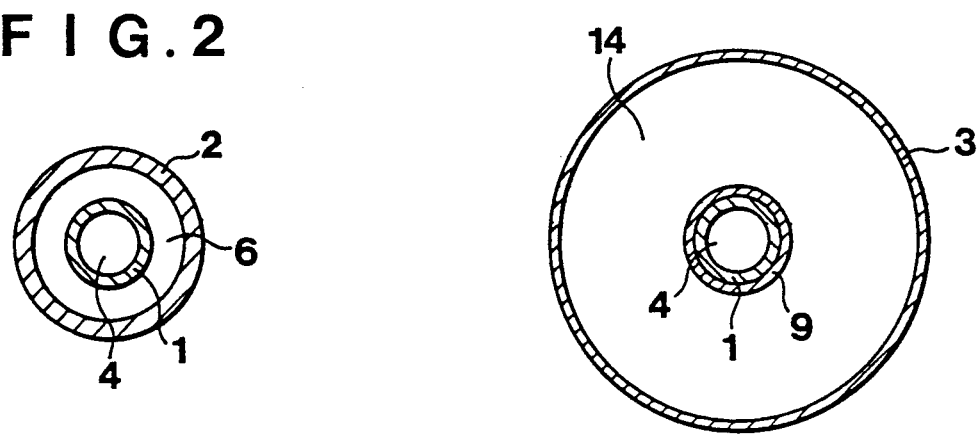

BALLOON CATHETER

BACKGROUND OF THE INVENTION

1. Field of the Invention

This invention relates to a balloon catheter. More particularly, it relates to a balloon catheter for expanding and thereby remedying stenosis in a blood vessel for improving the state of the distal side blood stream.

2. Description of the Prior Art

In the event of stenosis or obturations in the vascular system, such as blood vessels, percutaneous transuminal angioplasty (PTA) or percutaneous transluminal coronary angioplasty (PTCA) is performed for enlarging or recanalizing the narrowed or obturated site of the vascular system to thereby improve the body liquid stream towards the distal side of the vascular system. In PTA or PTCA, after a blood vessel is procured percutaneously, a fine guide wire is passed through the vessel. A catheter having an end balloon (expandable member) is introduced into the vessel, using this guide wire as the guide, until the balloon is positioned at the site of lesion where stenosis or obturation has occurred. A liquid such as contrast medium is injected continuously into the balloon via an end hub under a pressure of several to ten atmospheres for dilating the balloon towards the inner wall of the blood vessel for pressuring and thereby enlarging the narrowed or obturated sites.

As a balloon catheter employed in PTA or PTCA, there is known a balloon catheter having a coaxial dual tube system including an inner tube opened at one end and defining a first lumen and an outer tube surrounding the inner tube, forming a second lumen with the inner tube and provided with a distal balloon, or one in which a tubular member defining a lumen is provided with a distal balloon surrounding the end of the tubular member.

In the case of the former balloon catheter having the coaxial dual tube system, ring markers formed of an X-ray opaque material are provided at predetermined portions of the inner tube in the balloon that are substantially in register with both ends of the balloon., these ring markers being used as means for identifying the cylindrical portion of the balloon under X-ray fluoroscopy. However, considering that the balloon catheter is caused to proceed through the inside of the blood vessel presenting acute bend or bends, the risk is high that the inner tube disposed within the balloon at the bends of the blood vessel be broken and collapsed the lumen opened at one end the lumen opened at one end to obstruct smooth progress of the guide wire.

For overcoming the above difficulties, there is also known a balloon catheter in which a piping having at both ends thereof prescribed portions substantially in register with both ends of the cylindrical portion of the balloon is provided on the inner tube disposed within the balloon. While it is possible with this known balloon catheter to prevent the inner tube from being broken and collapsed, it is difficult for the balloon catheter to proceed through the inside of the blood vessel presenting acute bend or bends. Even supposing that the balloon catheter should have succeeded in proceeding beyond the bend, the risk is high that the piping remains bent to obstruct the progress thereof the blood vessel beyond the bend towards the distal side of the vascular system.

OBJECT AND SUMMARY OF THE INVENTION

It is a principal object of the present invention to provide a balloon catheter which is free from the above problems of the prior art and which is able to prevent breaking of the inner tube and obstructing of the lumen in blood vessels presenting an acute bend or bends.

According to the present invention, there is provided a balloon catheter comprising a tubular body including at least one lumen, and a foldable balloon provided at a predetermined forward portion on the outer surface of said tubular body so that the balloon communicates with at least one lumen in said tubular body, wherein the improvement resides in that a reinforcement is provided at a predetermined portion on the outer surface of said tubular body surrounded by said balloon According to the present invention, the diameter of a portion of the balloon catheter which is introduced into the patient's body and which is formed by said tubular body and the folded balloon is not more than 2.7 mm.

It is preferred that the reinforcement be formed of an X-ray opaque material.

It is preferred that the X-ray opaque material be platinum, gold, tungstene or alloys thereof.

It is preferred that the opaque material be a silverpalladium alloy.

It is preferred that the reinforcement be a wire in the form of a coil and having a circular, rectangular or an elliptical cross-section.

It is also preferred that the wire of the coil is formed by a coil spring having turns thereof in intimate and tight contact with one another.

Alternatively, turns of the coil spring may be arranged thick in both end parts and thin in the intemediate part of the coil spring.

According to the present invention, the portions of the balloon catheter surrounded by the balloon may be prevented from being broken and collapsed, even when the catheter is proceeding through the inside of the blood vessel presenting acute bend or bends, so that the balloon catheter can be prceeded positively to the site of lesion in the blood vessel.

BRIEF DESCRIPTION OF THE DRAWINGS

The present invention will now be described with reference to the accompanying drawings in which FIG. 1 is an enlarged sectional view showing the distal end part of the balloon catheter according to a preferred embodiment of the present invention, FIG. 2 is a sectional view taken along line II—II of FIG. 1, FIG. 3 is a sectional view taken along line III—III of FIG. 1.

DESCRIPTION OF PREFERRED EMBODIMENTS

By referring to the accompanying drawings, certain preferred embodiments of a balloon catheter of the present invention including a tubular member having two lumens will be explained hereinbelow in detail.

Figure 4:
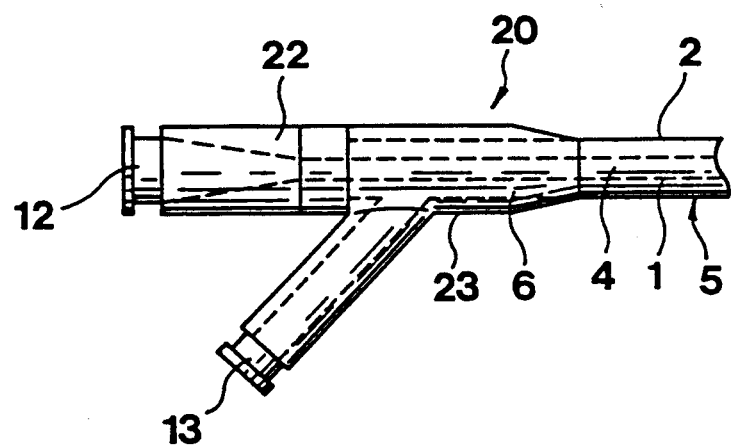
FIG. 4 is a diagrammatic view showing the proximal end part of the balloon catheter shown in FIG. 1.

FIGS. 1 to 4 illustrate a preferred embodiment of the balloon catheter according to the present invention. FIG. 1 is an enlarged sectional view showing the distal side of the balloon catheter. FIGS. 2 and 3 are sectional views taken along line II—II and line III—III of FIG. 1, respectively. FIG. 4 is an enlarged sectional view showing the proximal side of the balloon catheter.

As shown in FIGS. 1 to 4, the balloon catheter 10 of the present invention includes an inner tube 1 having a first lumen opened at one end, an outer tube 2 provided for encircling the inner tube 1 at a position set back a predetermined distance from a foremost part 1a of the inner tube 1 and defining a second lumen 6 between it and the outer surface of the inner tube 1, and a balloon 3 including a distal end 7 attached to the inner tube 1 and a proximal end 8 attached to the outer tube 2. The balloon 3 communicates with the second lumen in the vicinity of the proximal end 8. and has a cylindrical section 3a, can be including at least a portion thereof substantially cylindrical in contour to permit a constricted site of the blood vessel to be dilated easily. A reinforcement 9 is wound about a portion on the outer peripheral surface of the inner tube which is substantially in register with the cylindrical section 3a.

The balloon catheter 10 has the inner tube 1 and the outer tube 2 as a cathether tube or tubular body or member 5, the proximal end of which is provided with a bifurcated branched hub 20, as shown in FIG. 4. The branched hub 20 has a guide wire port 12 and an injection port 13 communicating with the first lumen 4 and with the second lumen 6, respectively.

The first lumen 4 formed by the inner tube 1 plays the role of a guide wire passage and a blood route or channel during use of the balloon catheter. The first lumen communicates at its proximal end with the guide wire port 12 formed in the branched hub 20, such that a guide wire 15 for the balloon catheter as later described is introduced into an opening end of the guide wire port 12 so as to be guided into the first lumen 4.

The inner tube 1 is preferably formed of a material exhibiting certain flexibility, including polyolefins, such as polyethylene, polypropylene, ethylene-propylene copolymers or ethylene-vinyl acetate copolymers, thermoplastic resins, such as polyvinyl chloride, polyamide elastomers or polyurethane, silicone rubber or latex rubber. More preferred are the aforementioned thermoplastic resins and most preferred are polyolefins.

The outer tube 2, in the inside of which the inner tube 1 is introduced, is preferably mounted coaxially with the inner tube 1 and at a position in which the foremost part of the outer tube is set back a small distance from the foremost part 1a of the inner tube 1. The second lumen 6 is defined between the inner surface of the outer tube 2 and the outer surface of the inner tube 1. The second lumen 6 plays the role of a channel for injection of, for example, contrast medium and dischaging of residual air and communicates at its proximal end with the injection port 13 of the branched hub 20. The second lumen 6 also communicates at its distal end with the inside of the balloon 3 at its rear end. The contrast medium, for example, are injected and charged into the internal space of the balloon 3 via the opening end of the injection port 13 and the second lumen 6 while the residual air is discharged simultaneously.

The outer tube 2 is preferably formed of a material exhibiting certain fexibility, including polyolefins, such as polyethylene, polypropylene, ethylene-propylene copolymers or ethylene-vinyl acetate copolymers, thermoplastic resins, such as polyvinyl chloride, polyamide elastomers or polyurethane, silicone rubber or latex rubber. More preferred are the aforementioned thermoplastic resins and most preferred are polyolefins.

The balloon 3 has its foremost part 7 and rear end 8 secured to the outer peripheral surface of the foremost part of the inner tube 1 and to the outer peripheral surface of the foremost part of the outer tube 2 liquid-tightly, respectively, as with an adhesive or by heat fusion, for delimiting an expansion space 14 between the inner surface of the balloon 3 and the outer surface of the inner tube 1. This expansion space 14 communicates at its rear end with the second lumen 6 along its overall periphery so that the contrast medium, for example, may be charged into the space 14 via the second lumen 6, as described hereinabove.

The balloon 3 may be folded in such a manner that, when the balloon is not dilated, it may be folded and wrapped about the outer periphery of the inner tube 1. In order that the constricted site of the blood vessel may be dilated more easily, at least a portion of the balloon 3 is formed as a substantially equidiametral cylinder for defining the aforementioned cylindrical section 3a. The cylindrical section need not be a true cylinder but may be in the form of a prism having a polygonal cross-section.

It should be noted that the balloon 3 is tapered from the forward side of the cylindrical section 3a to the foremost part 7 where it is secured to the inner tube 1 and from the rear side of the cylindrical section 3a to the rear end 8 where it is secured to the outer tube 2.

It should also be noted that, in the state in which the balloon 3 is folded and wrapped about the inner tube 1, that is, the balloon 3 is wrapped around the catheter tube 5, the portion of the balloon catheter introduced into the patient's body be of an outside diameter of not more than 2.7 mm at the maximum, since the balloon catheter can be used satisfactorily in such case in the body cavity, above all, in a finer vasculum.

The balloon 3 is preferably formed of a material exhibiting certain flexibility, including polyolefins, such as polyethylene, polypropylene, ethylene-propylene copolymers, ethylene-vinyl acetate copolymers or cross-linked ethylene-vinyl acetate copolymer, thermoplastic resins, such as polyvinyl chloride, polyamide elastomers or polyurethane, silicone rubber or latex rubber. More preferred are the aforementioned thermoplastic resins and most preferred are the cross-linked ethlene-vinyl acetate copolymers.

According to the present invention, a reinforcement 9 is wound about a predetermined portion of the outer surface of the inner tube 1 which is enclosed within the balloon 3, preferably the portion thereof in register with the aforementioned cylindrical section 3a. With the reinforcement 9 thus wound about the inner tube 1, the inner tube is rendered more resistant against buckling, so that there is no risk that the inner tube 1 disposed in the balloon 3 be broken or the first lumen 4 through which the guide wire 15 for the balloon catheter is passed be broken even at a bend of the blood vessel.

The reinforcement 9 is preferably formed of an X-ray opague material, preferably platinum, gold, tungsten or alloys thereof and more preferably a silver-palladium alloy, since a clear contrast image can then be obtained under X-ray fluoroscopy and thus the cylindrical section 3a of the balloon 3 can be identified more easily.

The reinforcement 9 is preferably a wire wound into a coil. By using the coil as the reinforcement, the inner tube 1 can be reinforced more strongly against buckling.

The wire of the coil preferably has a circular, rectangular or an elliptical cross-section for inceasing reinforcing effects.

The wire in the form of a coil may preferably be a spring coil so wound that its turns are in intimate contact with one another. With this dense winding of the wire, the inner tube can be reinforced more strongly against buckling.

The branched hub 20 is formed by an inner tube hub 22 and an outer tube hub 23. The inner tube hub 22 communicates with the first lumen 4, has a guide wire port 12 through which the guide wire 15 for the balloon catheter is introduced, and is secured to the inner tube 1. The outer tube hub 23 communicates with the second lumen 6, has an injection port 13 for injecting contrast medium, for example, and is secured to the outer tube 2.

The outer tube hub 23 and the inner tube hub 22 are secured to each other.

The branched hub 20 is preferably formed of thermoplastic resins, such as, for example, polycarbonate, polyamide, polysulfone, polyallylate or methacrylatebutylene-stylene copolymers.

For explaining the operation of the balloon catheter of the present invention shown in FIGS. 1 to 4, the method of using the balloon catheter in angioplasty (PTA or PCTA) will be explained by referring to FIGS. 5 to 10.

It is preferred that, before conducting to angioplasty by dilating and remedying constrictions occurred in the blood vessel, as much air as possible be removed from the inside of the balloon catheter. To this end, suction and injection means, such as a in-deflator, filled with contrast mediaum is attached to the injection port 13 of the catheter and the operation of alternate injection and suction is repeatedly performed to remove the air in the second lumen 6 and the balloon 3 to replace it with the contrast medium.

When the expansion space 14 of the balloon 3 and a space of the second lumen 6 is filled with the contrast medium and the residual air is removed completely, a predetermined amount of the contrast medium filled in the expansion space 14 is sucked and discharged by an injector fitted with a pressure gauge 24 to cause the balloon 3 to be wound about the inner tube 1 of the tubular member 5 to reduce the outside diameter of the balloon 3 so that the outside diameter of the portion of the balloon catheter 10 introduced into the patient's body is not more than 2.7 mm, in order to make ready for insertion of the balloon catheter into the blood vessel in angioplasty.

Figure 6:
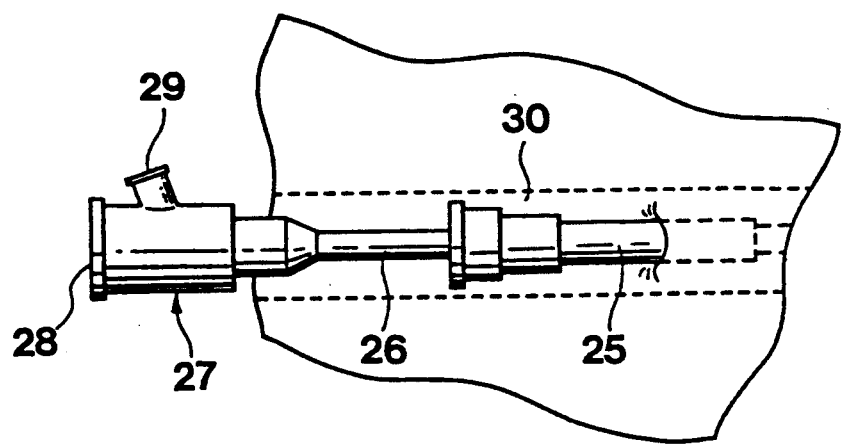
FIGS. 6 to 10 are diagrammatic views for illustrating the operation of the balloon catheter shown in FIG. 1, FIGS. 11 and 12 are enlarged sectional views showing the distal end part of balloon catheters according to modified embodiments of the present invention.
Figure 7:
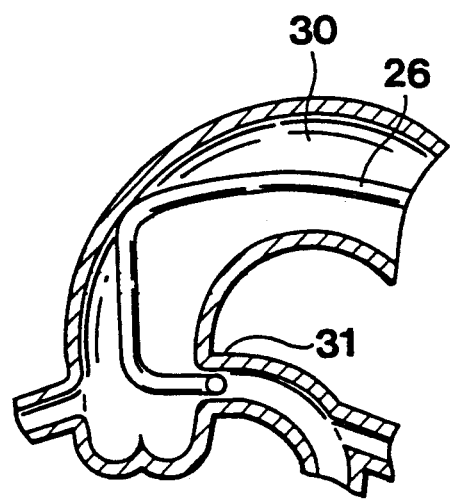

For angioplasty, a blood vessel 30 is procured, that is, peirced with the dilater and sheath 25 as shown in FIG. 6( by relying upon, for example, the Sheath method. A guiding catheter indwelled gauide wire is prepared. A guiding catheter 26 is introduced into the blood vessel 30 along the guide wire and left at an inlet 31 to the coronary artery having a target lesion. The guide wire for the guide catheter is then removed.

Figure 5:
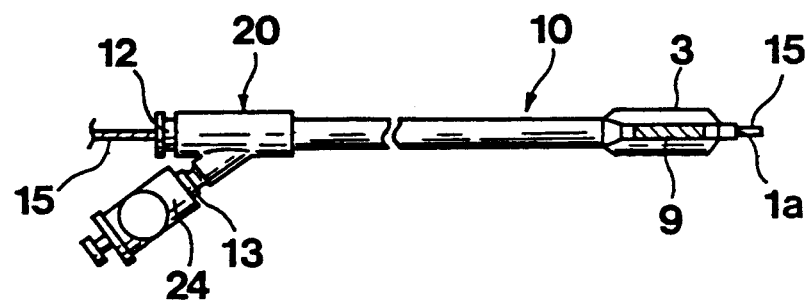
FIG. 5 is an overall side view showing the balloon catheter of FIG. 1, with a portion thereof being broken away.

The balloon catheter guide wire 15 is then introduced at the guide wire port 12 of the balloon catheter 10 into the inner tube 1 of the tubular member 5, that is, into the first lumen 4, until the guide wire is protruded several centimeters beyond the end opening 1a of the inner tube 1, as indicated in FIG. 5. The resulting assembly is then introduced into the guiding catheter 26 via a balloon catheter port 28 of a Y-shaped connector 27, to the proximal end of which the guiding catheter 26 is connected, as shown in FIG. 6. The balloon catheter 10 is then proceeded through the inside of the guiding catheter 26 so as to be proceeded via the forward end of the guiding catheter 26 into the blood vessel 30 having the target lesion 30.

Figure 8:
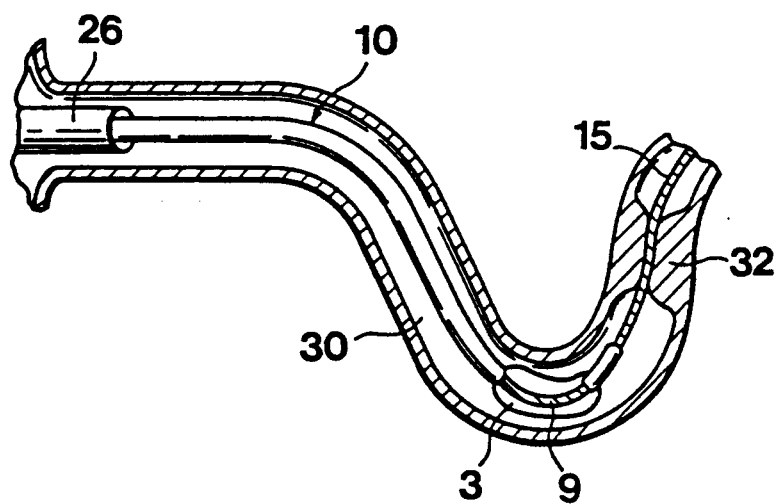

The balloon catheter guide wire 15 is then extended to the target lesion through the inside of the blood vessel 30, as shown in FIG. 8. The guide wire 15 is left in the blood vessel after it has passed through the constricted site 32.

The balloon catheter 10 is then advanced through the inside of the blood vessel 30 along the balloon catheter guide wire 15. The balloon catheter 10 of the present invention has an increased resistance against bending since the reinforcement 9 is wound about the portion of the outer surface of the inner tube 1 disposed within the balloon 3, so that, even when the blood vessel 30 has an acute bend, as shown in FIG. 8, there is no risk of obstruction of the progress of the balloon catheter guide wire 15 caused by the breaking of the inner tube 1 within the balloon 3 or the collapse of the first lumen opened at the end and hence the balloon catheter 10 can be proceeded smoothly towards the lesion at the distal side.

It should be noted that, when the reinforcement 9 is formed as a wire in the form of a coil, above all, as a coil spring, which is wound about the outer surface of the inner tube 1 with the neighboring turns of the coil in tight and intimate contact with one another, an increased resistance is obtained against external forces.

When the coil wire has an elliptical, rectangular or a circular cross-section, a further increase is obtained in the resistance against external forces.

Also, when the reinforcement 9 is formed of an X-ray opague material, the reinforcement 9 is indicated as a clear X-ray contrast image, under X-ray fluoroscopy, such that this reinforcement 9 can be checked visually as an indicia for the balloon for positively positioning the cylindrical section 3a of the balloon 3 at the stenosis site 32.

It is preferred that the X-ray opague material be platinum, gold, tungstene, alloys thereof or a silverpalladium alloy, since then a clearer X-ray contrast image is produced and thus the reinforcement may be used more effectively as the indicia for the balloon 3.

It is also preferred that, in the state in which the balloon 3 is folded and wrapped about the inner tube 1, that is, about the tubular member 5, the portion of the balloon catheter introduced into the patient's body be of an outside diameter of not more than 2.7 mm, since then the balloon catheter can be used more advantageously within the body cavity, above all, within the vessel having a narrower inner cavity.

Figure 9:
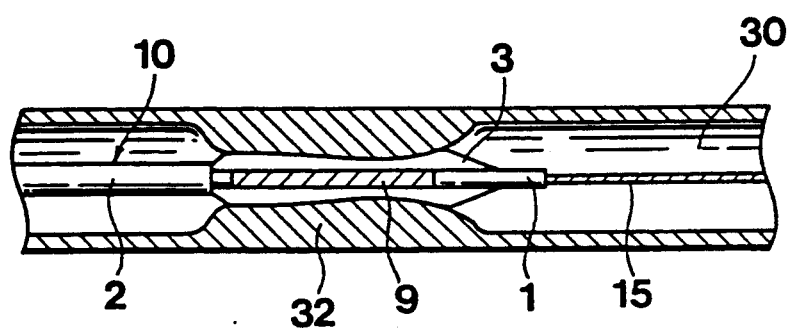
Figure 10:
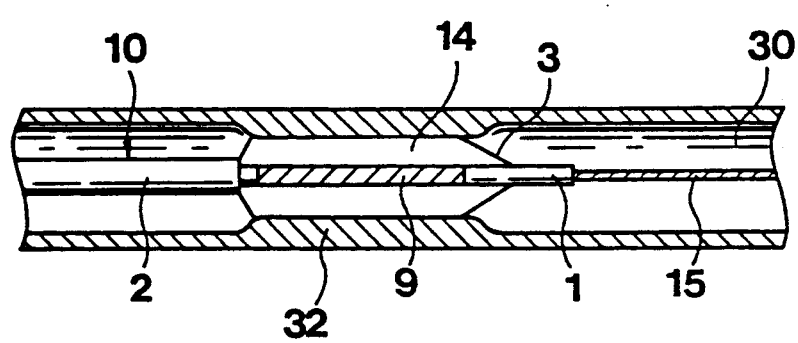

When the balloon 3 reaches the stenosis site 32, as shown in FIG. 9, the contrast medium are injected into the dilated space 14 of the balloon 3, as the contrast medium are pressurized to several to ten and odds atmospheres, by the injector fitted with a pressure gauge 24, connected to the injection port 13 of the balloon catheter 10, for expanding the balloon 3 as shown in FIG. 10 for pressuring and enlarging the diameter of the stenosis site 32.

After termination of this operation, the contrast medium are injected into the blood vessel via contrast medium injection port 29 of the Y-shaped connector 27 connected to the proximal end of the guiding catheter 26 for visual checking of the distal side blood stream by X-ray fluoroscopy. When it is observed that the blood stream is improved, the balloon catheter 10 and the balloon catheter guide wire 15 are removed from the blood vessel 30. The guiding catheter 26 is then removed and the pierced portion of the blood vessel is pressed to stop the hemorrhage to terminate the operation.

The above described balloon catheter is formed by coaxially arranged inner and outer tubes defining two lumens. However, the present invention may naturally be applied to a balloon catheter formed by a tubular member defining a sole lumen.

Figure 11:
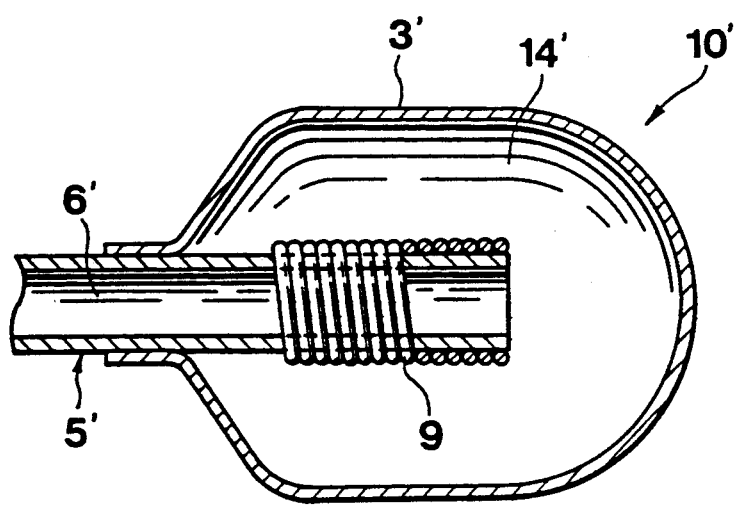

Referring to FIG. 11, showing a second embodiment of the present invention, a balloon 3' enclosing the distal part of a tubular member 5' is provided at the distal part of the tubular member 5' defining the sole lumen 6'. The reinforcement 9 may be provided at the distal part of the tubular member 5' surrounded by the balloon 3' for forming a balloon catheter 10'.

This balloon catheter 10' is used for improving the state of stenosis of the coronary artery, for example. The operation of the balloon catheter 10' is basically the same as that of the above described balloon catheter 10 having the dual tube structure. However, in the present embodiment, the balloon catheter guide wire 15 is introduced into the lumen 6' at its proximal end and held so that its distal part does not break the balloon 3'. In this state, the air inside the balloon 3' is replaced by the contrast medium in the same way as in the preceding embodiment. The contrast medium are then sucked and discharged in a predetermined amount using the aforementioned in-deflator to cause the balloon 3' to be wrapped about the tubular member 5' to reduce the outside diameter of the balloon 3' so that the outside diameter of the portion introduced into the balloon catheter 10' is not more than 2.7 mm.

Figure 12:
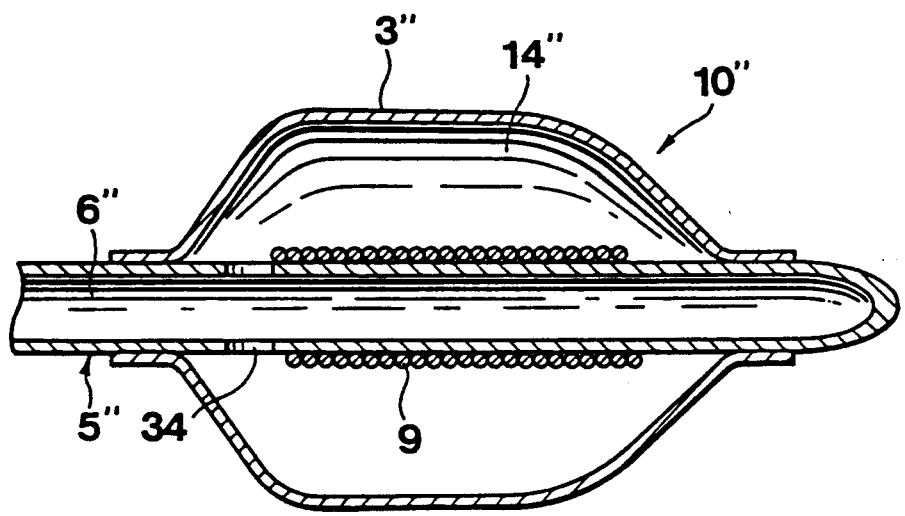
Figure 13:
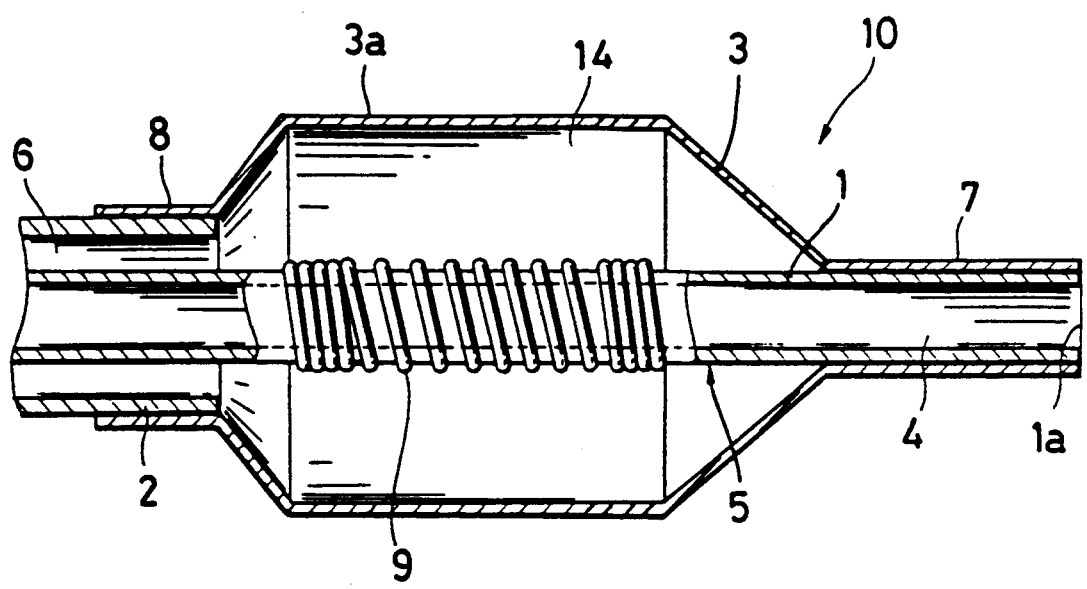
FIG. 13 shows a modification of the embodiment of FIG. 1.

Referring to FIG. 12, illustrating a third embodiment of the present invention, a tubular member 5" defining a sole lumen 6" has a distal closed end. At the distal part of the tubular member 5" is provided a balloon 3" enclosing the distal part of the tubular member 5". The lumen 6" of the tubular member 5" may be in fluid communication with an expansion space 14" of the balloon 3" through an orifice or orifices formed in the tubular member 5". The reinforcement 9 may be provided at the distal part of the tubular member 5" surrounded by the balloon 3" and have turns therof so wound that they be in intimate contact with each other. The operation of this balloon catheter is substantially same as those of the above-discribed balloon catheters.

In case of the reinforcement being a coil spring, it may alternatively be so wound that its turns are thick for example in intimate contact with each other in both end parts and thin or sparse in the intermediate part of the coil spring.

The balloon catheter in this state is introduced into the blood vessel 30, as it is guided by the balloon catheter guide wire 15, until the balloon 3' reaches the stenosis site 32 in the same way as in the preceding embodiment. The contrast medium are then injected in a predetermined amount into the expansion space 14' of the balloon 3', with the aid of the pressure gauge-injector 24, for dilating the balloon 3' for pressuring and enlarging the stenosis 32.

When it is observed that the state of the blood stream is improved, the balloon catheter 10' may be removed from the inside of the blood vessel, as described hereinabove.

In the present second embodiment, by providing the reinforcement 9 at the forward side of the tubular member 5', the tubular member can be reinforced against buckling.

EFFECT OF THE INVENTION

As described in detail, the present invention provides a balloon catheter comprising a tubular body including at least one lumen, and a foldable balloon provided at a predetermined distal portion on the outer surface of said tubular body so that the balloon communicates with at least one lumen in said tubular body, wherein a reinforcement is provided at a predetermined portion on the outer surface of said tubular body surrounded by said balloon.

With the above described arrangement of the balloon catherter, the balloon portion of the balloon catherter may positively be proceeded to the target lesion, without breaking and collapsing of the tube portion enclosed in the balloon even at progress through an acute bend of the blood vessel.

What is claimed is:

1. A balloon catheter, comprising:
   a tubular body including at least one lumen;
   a foldable balloon provided at a predetermined distal portion of said tubular body and surrounding the outer surface off said distal portion of said tubular body so that said balloon communicates with said at least one lumen of said tubular body;
   a coil spring provided at a predetermined portion on the outer surface of the portion of said tubular body surrounded by said balloon, for reinforcing said tubular body, said coil spring having opposite end portions and an intermediate portion, said coil spring being wound such that the turns thereof are in intimate contact with each other at both end portions thereof and are sparse in said intermediate portion thereof.

2. The balloon catheter of claim 1, wherein the outside diameter of a portion of the catheter to be introduced into a patient's body which is formed by said tubular body and said folded balloon is not more than 2.7 cm.

3. The balloon catheter of claim 1, wherein said coil spring is formed of an X-ray opaque material.

4. The balloon catheter of claim 3, wherein said X-ray opaque material is selected from the group consisting of platinum, gold, tungsten, and alloys thereof.

5. The balloon catheter of claim 3, wherein said X-ray opaque material is a silver-palladium alloy.

6. The balloon catheter of claim 1, wherein said coil spring is formed from a wire having a circular cross-section.

7. The balloon catheter of claim 1, wherein said coil spring is formed from a wire having a rectangular cross-section.

8. The balloon catheter of claim 1, wherein said coil spring is formed from a wire having a ellipsoidal cross-section.

9. The balloon catheter of claim 1, wherein said tubular body has at least two lumens.

10. The balloon catheter of claim 9, wherein at least one of said lumens is open at said distal end of said tubular body.

11. The balloon catheter of claim 1, wherein said tubular body has a single lumen.

12. The balloon catheter of claim 11, wherein said tubular member defining said single lumen is closed at its distal end.

13. The balloon catheter of claim 11, wherein said tubular member defining said single lumen is open at its distal end.

* * * * *

UNITED STATES PATENT AND TRADEMARK OFFICE
CERTIFICATE OF CORRECTION

PATENT NO. : 4,994,032
DATED : February 19, 1991
INVENTOR(S) : Yoshiaki SUGIYAMA et al It is certified that error appears in the above-identified patent and that said Letters Patent is hereby corrected as shown below:

Column 5, line 11, Change "inceasing" to --increasing--.

Column 5, line 64, Change "gauide" to --guide--.

Title page, item [57] col. 2,
In the Abstract, line 9, Change "on" to --of--.

In the Abstract, line 9, Change "opague" to --opaque--.

Signed and Sealed this

Twenty-second Day of August, 1995

Attest:

BRUCE LEHMAN

*Attesting Officer*    Commissioner of Patents and Trademarks